United States Patent
Lee et al.

(10) Patent No.: US 9,427,368 B2
(45) Date of Patent: Aug. 30, 2016

(54) APPARATUS FOR AUTOMATICALLY TREATING EXCREMENT AND CONTROLLING METHOD THEREOF

(75) Inventors: Jong Chan Lee, Anyang (KR); Ho Sang Lee, Seoul (KR)

(73) Assignee: CURACO INC., Seoul (KR)

( * ) Notice: Subject to any disclaimer, the term of this patent is extended or adjusted under 35 U.S.C. 154(b) by 867 days.

(21) Appl. No.: 13/640,043

(22) PCT Filed: Apr. 6, 2011

(86) PCT No.: PCT/KR2011/002404
§ 371 (c)(1),
(2), (4) Date: Oct. 8, 2012

(87) PCT Pub. No.: WO2011/126297
PCT Pub. Date: Oct. 13, 2011

(65) Prior Publication Data
US 2013/0036544 A1     Feb. 14, 2013

(30) Foreign Application Priority Data

Apr. 8, 2010  (KR) .................. 10-2010-0032264
Apr. 8, 2010  (KR) .................. 10-2010-0032279

(51) Int. Cl.
*A61G 9/00*   (2006.01)
*A61F 5/451*  (2006.01)

(52) U.S. Cl.
CPC .............. *A61G 9/003* (2013.01); *A61F 5/451* (2013.01); *A61G 9/006* (2013.01)

(58) Field of Classification Search
CPC ...... A61F 5/451; A61G 9/003; A61G 9/006; A61G 9/00

USPC ........................ 4/443–448, 450–457, 661
See application file for complete search history.

(56) References Cited

U.S. PATENT DOCUMENTS

| | | | | |
|---|---|---|---|---|
| 5,363,514 A | * | 11/1994 | Lee ................................ | 4/455 |
| 5,681,297 A | * | 10/1997 | Hashimoto et al. .......... | 604/355 |
| 5,702,536 A | * | 12/1997 | Carruth ......................... | 134/10 |
| 5,809,586 A | * | 9/1998 | Kitamura ....................... | 4/443 |
| 6,110,159 A | * | 8/2000 | Tsujita et al. ................. | 604/387 |

(Continued)

FOREIGN PATENT DOCUMENTS

| JP | 2002-113052 A | 4/2002 |
|---|---|---|
| JP | 2004-329715 A | 11/2004 |

(Continued)

OTHER PUBLICATIONS

International Search Report for PCT/KR2011/002404 filed on Oct. 13, 2011.

*Primary Examiner* — Paul R Durand
*Assistant Examiner* — William R Klotz

(57) ABSTRACT

An apparatus for automatically treating the excrement comprises a mounting unit, a control device unit, and a washing water supply path which is connected from the washing water supply part to the mounting unit. The washing water supply part comprises a washing water storage tank in which the washing water is stored. A pump is operated in a forward or in a reverse direction to supply the washing water of the washing water storage tank to the mounting unit, or collecting the residual washing water in the washing water supply path to the washing water storage tank. An instantaneous water heater provides on the washing water supply path to heat the washing water a control portion which controls the operations of the pump in the forward direction or the reverse direction.

18 Claims, 9 Drawing Sheets

(56) References Cited

U.S. PATENT DOCUMENTS

| | | | |
|---|---|---|---|
| 9,032,563 B2* | 5/2015 | Lee | 4/450 |
| 2008/0004576 A1* | 1/2008 | Tanaka et al. | 604/317 |
| 2008/0178377 A1* | 7/2008 | Liu | 4/450 |
| 2009/0193571 A1* | 8/2009 | Nakamura et al. | 4/300 |
| 2011/0265889 A1* | 11/2011 | Tanaka et al. | 137/386 |

FOREIGN PATENT DOCUMENTS

| | | |
|---|---|---|
| JP | 2008-149042 A | 7/2008 |
| JP | 2008-161490 A | 7/2008 |
| KR | 10-2008-0000414 A | 1/2008 |
| KR | 10-0924812 B1 | 11/2009 |
| KR | 10-2010-0030352 A | 3/2010 |

* cited by examiner

APPARATUS FOR AUTOMATICALLY TREATING EXCREMENT AND CONTROLLING METHOD THEREOF

TECHNICAL FIELD

The present invention relates to an apparatus for automatically treating excrement capable of receiving excrement of a patient and automatically treating the excrement and a controlling method thereof, and more particularly, to an apparatus for automatically treating excrement which can spray warm washing water from an initial washing operation in a bidet and easily perform a drainage processing on the residual washing water in a washing water storage tank for separation or storage of an apparatus, and a controlling method thereof. Further, the present invention relates to an apparatus for automatically treating excrement which reduces a load of a pump for sucking excrement and air, improves filtering performance of a filter unit, and has a structure in which a filter is easily replaced by simplifying a coupling structure of the filter unit.

BACKGROUND ART

An excrement treating apparatus which can automatically treat excrement generally for patients who cannot independently treat excrement due to having a surgical operation, and the like, in a hospital or the aged who cannot move freely has been developed.

The excrement treating apparatus includes a mounting unit having a shape of a diaper to surround hips of a patient so as to receive excrement of a patient, and a control device unit for making a control so as to vacuum suck and then store the excrement of the mounting unit or supply washing water or washing air for washing the excrement and a bidet to the mounting unit.

The control device unit includes a washing water storage tank in which the washing water is stored, a pump which pressurizes the washing water of the washing water storage tank and supplies the pressurized washing water to the mounting unit, and an instantaneous water heater which heats the washing water supplied to the mounting unit to a warm state.

Further, a path connection member for detachably connecting connection tubes, such as an excrement suction line, a supply line of the washing water and the washing air, and a bidet nozzle line, to the mounting unit is mounted on the control device unit.

However, in the excrement treating apparatus in the related art, in an initial washing operation stage in the bidet, the residual washing water in a washing water supply path between the bidet nozzle and the instantaneous water heater is sprayed through the bidet nozzle in a cold state without passing through the instantaneous water heater, so that there is a problem of giving an unpleasant feeling to a user.

Further, when a connector of connection tubes between the mounting unit and the path connection member is separated to replace the mounting unit in a case where the excrement treating apparatus is moved or stored or a patient is changed, there is a problem in that the residual washing water in the connection tubes is poured into a floor, so that a neighboring environment becomes dirty.

In the meantime, when the excrement treating apparatus is not used and is stored, it is necessary to withdraw a water tank which is inserted in the washing water storage tank to the outside, and drain and dry the stagnant washing water at the bottom of an inside of the washing water storage tank in order to prevent the propagation of bacteria and generation of decomposition in the washing water storage tank.

However, the excrement treating apparatus in the related art has a structure in which the stagnant washing water in the washing water storage tank is not easily drained, so that there is a problem in that a lot of time and effort is needed for a drying operation of the washing water storage tank.

Further, in the related art, one commercially available pump is used in order to supply the washing water of the washing water storage tank to the mounting unit, but there is a problem in that a gushing pressure of the washing water is at a lower level than an appropriate level, so that washing efficiency is deteriorated, and a lot of expense is consumed to develop a separate dedicated pump appropriate to be applied to the excrement treating apparatus in order to increase a gushing pressure of the washing water.

In the meantime, the control device unit includes an excrement storage unit which sucks the excrement through the excrement suction line and then stores the excrement, a filter unit connected to the excrement storage unit to purify the sucked air, and an excrement suction unit connected to the filter unit to provide suction force for vacuum suction of the excrement.

Filtering performance of the filter unit is determined according to a contact area and a time in and at which foreign substances are collected in a filter. In the related art, the filter unit having a structure in which a filter is elongated in a flow direction of air passing the filter in order to obtain the purified air in which the foreign substances and smell are removed by maximally filtering the foreign substances included in the sucked air is used.

However, when the filter is elongated as described, the pressure loss of the air is increased, so that there is a problem in that a load of a motor for operating a pump of the excrement suction unit is increased in order to obtain a desired degree of vacuum.

Further, although the filter unit of the excrement treating apparatus includes consumable components which need to be replaced after the use for a predetermined time, a coupling structure of the components included in the filter unit is complex in the related art, so that there is a problem in that it is difficult and it takes much time to replace the components.

DISCLOSURE

Technical Problem

The present invention has been made in order to solve the problems, and an object of the present invention is to provide an apparatus for automatically treating excrement which can supply heated warm washing water from an initial washing operation in a bidet, and a controlling method thereof.

Another object of the present invention is to provide an apparatus for automatically treating excrement which can prevent water from being poured from a connection portion even though the mounting unit is separated from the connection tubes for connecting a path connection member when the apparatus for treating excrement is moved or stored, or a user is changed, and a controlling method thereof.

Another object of the present invention is to provide an apparatus for automatically treating excrement in which a drainage processing is easily performed on stagnant washing water inside a washing water storage tank when the apparatus is stored, and a controlling method thereof.

Another object of the present invention is to provide an apparatus for automatically treating excrement which can reduce a load of a pump used for suction of excrement and air and improve filtering performance.

Another object of the present invention is to provide an apparatus for automatically treating excrement having a coupling structure in which a filter that is a consumable component is easily replaced.

Another object of the present invention is to provide an apparatus for automatically treating excrement which is configured such that a constituent component of a filter unit is separable in order to easily replace a filter, and can prevent a leakage of air from a separated boundary portion.

Another object of the present invention is to provide an apparatus for automatically treating excrement which can automatically prevent a worker from being directly exposed to light of an ultraviolet lamp included in a filter unit during a replacement operation of a filter.

Technical Solution

In order to accomplish the aforementioned object, the present invention provides an apparatus for automatically treating excrement including a mounting unit 1 for receiving excrement of a patient, a control device unit 2 including a washing water supply unit 50 configured to supply washing water for washing excrement and a bidet to the mounting unit 1, and a washing water supply path connected from the washing water supply unit 50 to the mounting unit 1, the washing water supply unit 50 including: a washing water storage tank 51 in which the washing water is stored; pumps 52 operated in a forward direction so as to supply the washing water of the washing water storage tank 51 to the mounting unit 1, or operated in a reverse direction so as to collect the residual washing water inside the washing water supply path to the washing water storage tank 51; an instantaneous water heater provided on the washing water supply path to heat the washing water supplied to the mounting unit 1; and a controller configured to control the pump 52 to be operated in the forward direction or the reverse direction, the controller instantly controlling the pump 52 to be operated in the forward direction when the excrement is detected in the mounting unit 1, and controlling the pump 52 to be operated in the reverse direction for a set time so as to collect the residual washing water in the washing water supply path before the instantaneous water heater 53 after an operation of treating the excrement is completed.

Further, the apparatus for automatically treating excrement may further include an excrement receiving unit 10 for receiving the excrement of the patient, an excrement storage unit 20 configured to suck the excrement of the excrement receiving unit 10 through an excrement suction line 61 and then store the sucked excrement, a filter unit 30 connected to the excrement storage unit 20 and configured to purify sucked air, and an excrement suction unit 40 connected to the filter unit 30 and configured to provide suction force for vacuum sucking the excrement, in which the filter unit 30 includes: an upper cover 310 including a coupler 25 communicated with the excrement storage unit 20; a first filter unit 320 including activated carbon filled therein so that pollutants are collected while air introduced through the coupler 25 passes through; a second filter unit 330 configured to filter dust of the activated carbon contained in air passing through the first filter unit 320; a main body 340 having an upper part opened/closed by the upper cover 310, accommodating the first filter unit 320 and the second filter unit 330 therein, and having an opened lower part; and a bottom frame 350 on which the main body 340 is seated, the bottom frame 350 including ultraviolet lamps 351 for sterilizing the air passing through the second filter unit 330.

A method of controlling an apparatus for automatically treating excrement of the present invention, the apparatus including a mounting unit 1 for receiving excrement of a patient, a control device unit 2 including a washing water supply unit 50 configured to supply washing water for washing excrement and a bidet to the mounting unit 1, and a washing water supply path connected from the washing water supply unit 50 to the mounting unit 1, includes operating pumps 52 included in the washing water supply unit 50 in a reverse direction of a supply direction of the washing water for a set time after an operation of treating the excrement is completed, and collecting the residual washing water in a washing water supply path connected from the mounting unit 1 to the washing water storage tank 51 before an instantaneous water heater 53 provided on the washing water supply path.

Advantageous Effects

According to the present invention, the pumps are operated in a reverse direction of a water supply direction for a set time after an operation of treating excrement is completed, so that the cold washing water stagnant in the washing water supply path is collected before the instantaneous water heater to become in a standby state, and the pumps are instantly operated in a water supply direction when the excrement is detected in the excrement receiving unit of the mounting unit, so that the washing water for excrement washing and bidet washing is supplied to the mounting unit, and thus there is an advantage in that a heated warm washing water may be supplied by making washing water pass through the instantaneous water heater from an initial washing operation in the bidet.

Further, there is an advantage in that when the apparatus for treating excrement is moved or stored, or the mounting unit is replaced because a user is changed, the residual washing water in the washing water supply path is collected before the instantaneous water heater, so that it is possible to prevent a neighboring environment from becoming dirty caused by overflow of the washing water even though a connector of the connection tubes is separated from a path connection member.

Further, there is an advantage in that the drain line returning to the washing water storage tank is provided on the washing water supply line, so that the drainage processing may be easily performed on the stagnant washing water in the washing water storage tank, and the pumps are arranged in a dual parallel structure, so that gushing pressure of the washing water is increased by using a commercially available pump even without newly developing a separate dedicated pump, thereby improving cleaning power.

Further, a thickness of the filter unit through which the air passes is formed to be short in a path direction of the air and an area of the filter unit through which the air passes is formed to be wide, so that a time for which pollutants are collected in activated carbon increases by decreasing flow velocity by which the air passes and pressure loss, thereby being capable of reducing a load of the pump for providing suction force and improving filtering performance of the filter.

Further, there is an advantage in that a coupling structure between the constituent components inside the filter unit is simplified, so that the filter is easily replaced.

Further, there is an advantage in that the flow of the air is induced so that the air introduced in the filter unit sequentially passes through the first filter unit and the second filter unit even while a structure in which the first filter unit and the second filter unit are accommodated inside the main body is simply configured.

Further, when the main body is separated from the bottom frame during the replacement operation of the filter, the power supplied to the ultraviolet lamp is automatically blocked, so that there is an effect in that direct irradiation of light of the ultraviolet lamp harmful to a human body to an operator may be prevented in advance.

MODE FOR CARRYING OUT THE INVENTION

Hereinafter, a configuration and an operational effect of an exemplary embodiment of the present invention will be described in detail with reference to the accompanying drawings.

Figure 1:
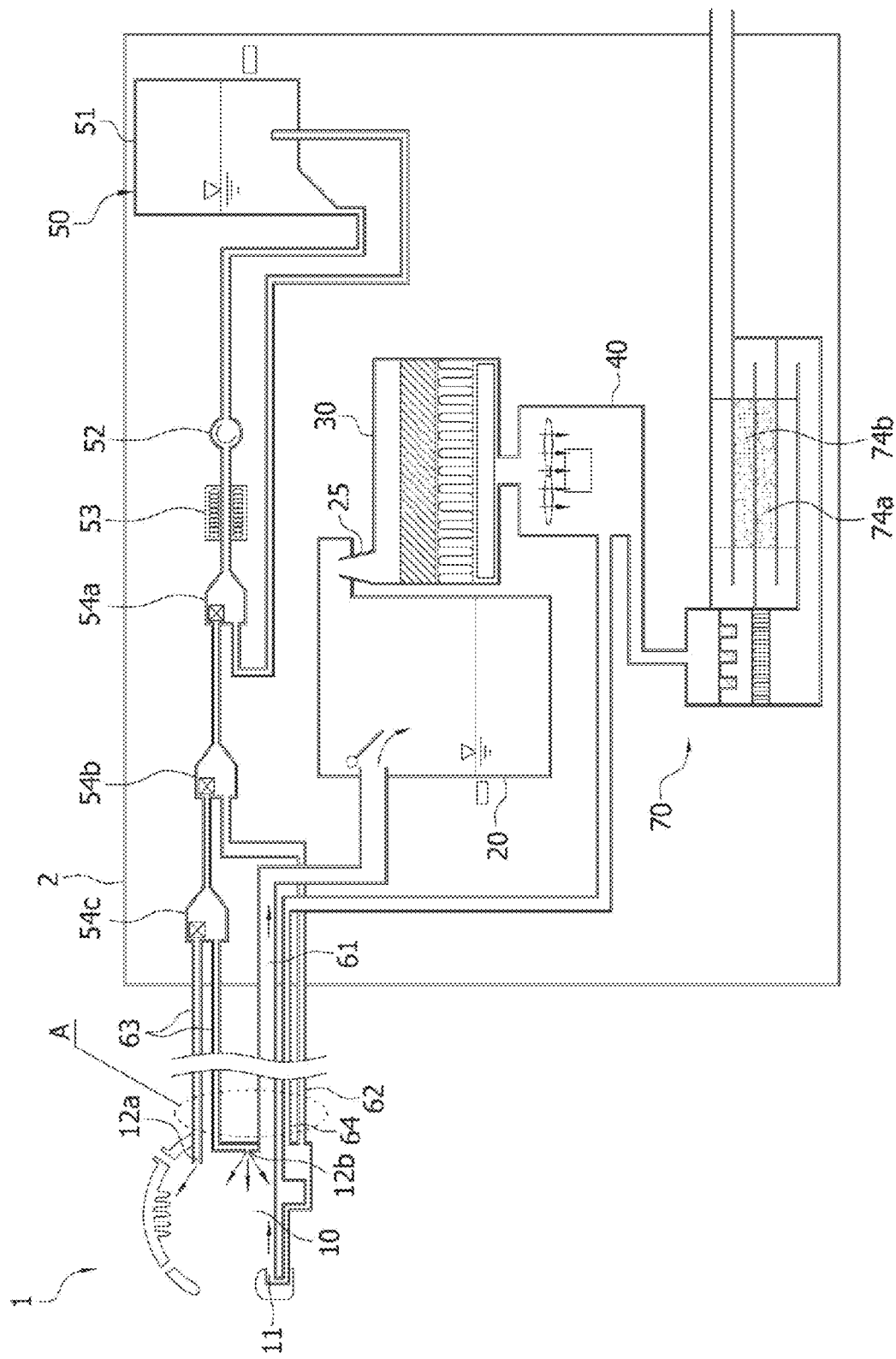
FIG. 1 is a diagram schematically illustrating an apparatus for automatically treating excrement according to the present invention.

FIG. 1 is a diagram schematically illustrating an apparatus for automatically treating excrement according to the present invention.

The apparatus for automatically treating excrement of the present invention includes a mounting unit 1 for receiving excrement of a patient, and a control device unit 2 for controlling so as to vacuum suck and then store the excrement of the mounting unit 1 or supply washing water and washing air to the mounting unit 1.

The mounting unit 1 includes an excrement receiving unit 10 in which the excrement of the patient is stagnant, a washing water spray nozzle 11 for spraying a mixture of the air and the washing water toward the excrement receiving unit 10, and bidet nozzles 12a and 12b for spraying the washing water toward the anus and genital area of the patient in an inside thereof.

The control device unit 2 includes an excrement storage unit 20 for sucking and then storing the excrement of the excrement receiving unit 10 through an excrement suction line 61, a filter unit 30 connected to the excrement storage unit 20 to purify the sucked air, an excrement suction unit 40 connected to the filter unit 30 to provide suction force for vacuum sucking the excrement, a washing water supply unit 50 for supplying the washing water for washing excrement and the bidet, and an air discharging unit 70 for making the air passing the excrement suction unit 40 pass through air filtering members 74a and 74b and then discharge the passed air to the outside.

The nozzles of the mounting unit 1 are connected with a path of the air and the washing water.

First, the washing water spray nozzle 11 is connected with a washing air supply line 64 connected to an outlet side of the excrement suction unit 40 and a washing water supply line 62 connected to the washing water supply unit 50. Accordingly, the air and the washing water are mixed, and then supplied to the washing water spray nozzle 11.

The bidet nozzles 12a and 12b include an upper bidet nozzle 12a and a lower bidet nozzle 12b, and are connected to a bidet nozzle line 63 connected to the washing water supply unit 50.

The excrement sucked by the suction force of the excrement suction unit 40 flows in the excrement storage unit 20 through the excrement suction line 61, and an internal space of the excrement storage unit 20 is connected with an inlet side of the filter unit 30 through a coupler 25.

The air in the internal space of the excrement storage unit 20 flows in the filter unit 30, so that the filter unit 30 removes foreign substances and smell and discharges purified air toward the excrement suction unit 40.

The excrement suction unit 40 includes a vacuum pump connected to an outlet side of the filter unit 30. The air discharged from the vacuum pump may be heated by a heater.

The washing water supply unit 50 includes a washing water storage tank 51 in which the washing water is stored, a pump 52 for supplying the washing water of the washing water storage tank 51 toward the mounting unit 1, an instantaneous water heater 53 for heating the washing water to a warm state, and a plurality of valves 54 for selectively supplying the washing water to any one of the washing water supply line 62 or the bidet nozzle line 63.

A portion indicated by "A" in FIG. 1 represents a path connection portion for connecting the plurality of tubes 61, 62, 63, and 64 between the mounting unit 1 and the control device unit 2.

Figure 2:
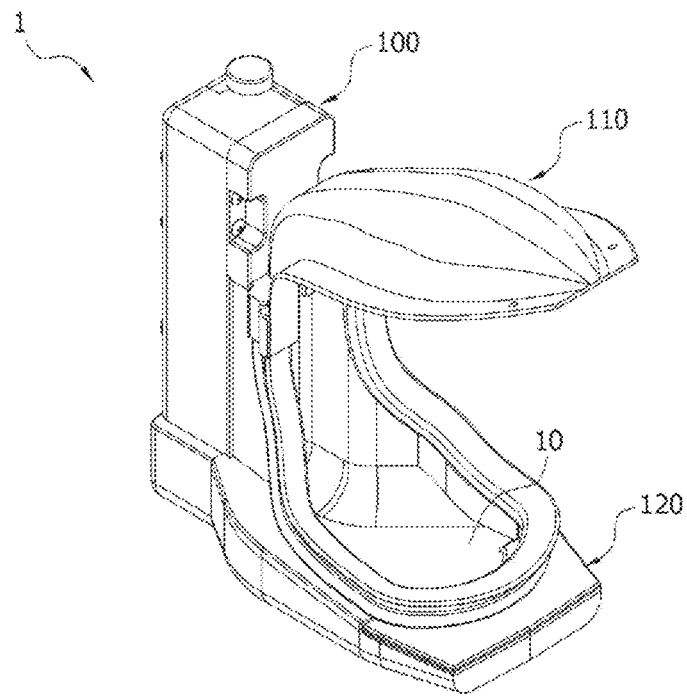
FIGS. 2 and 3 are perspective views illustrating a mounting unit of the present invention at different angles.
Figure 3:
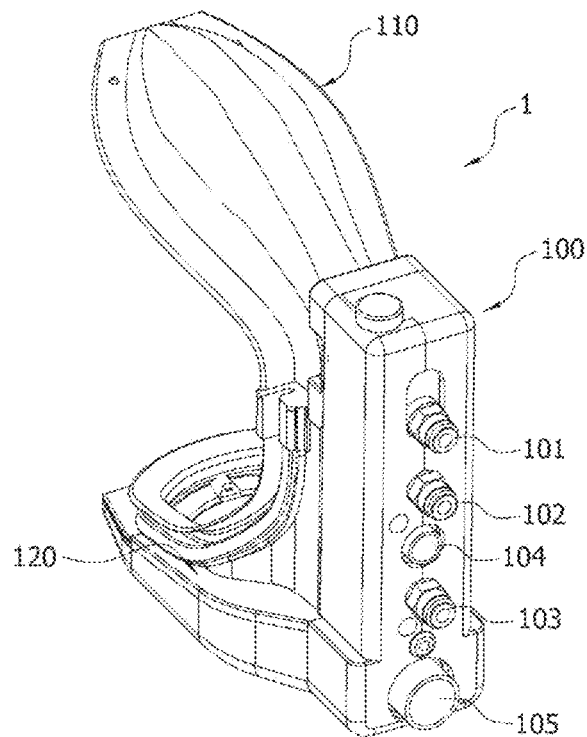

FIGS. 2 and 3 are perspective views illustrating the mounting unit of the present invention at different angles.

The mounting unit 1 includes a path connection unit 100 connected to the plurality of tubes 61, 62, 63, and 64 to provide a path of the washing water or the air to the path, a mounting member 110 installed in a front side of the path connection unit 110 so as to be in close contact with the hips of the patient and made of an elastic material, and an excrement storage main body 120 coupled to a lower part of the mounting member 110 to form the excrement receiving unit 10 so as to receive the excrement of the patient.

The path connection unit 100 includes first to fifth couplers 101, 102, 103, 104, and 105 connected with the excrement suction line 61, the washing water supply line 62, the bidet nozzle line 63, and the washing air supply line 64.

Figure 4:
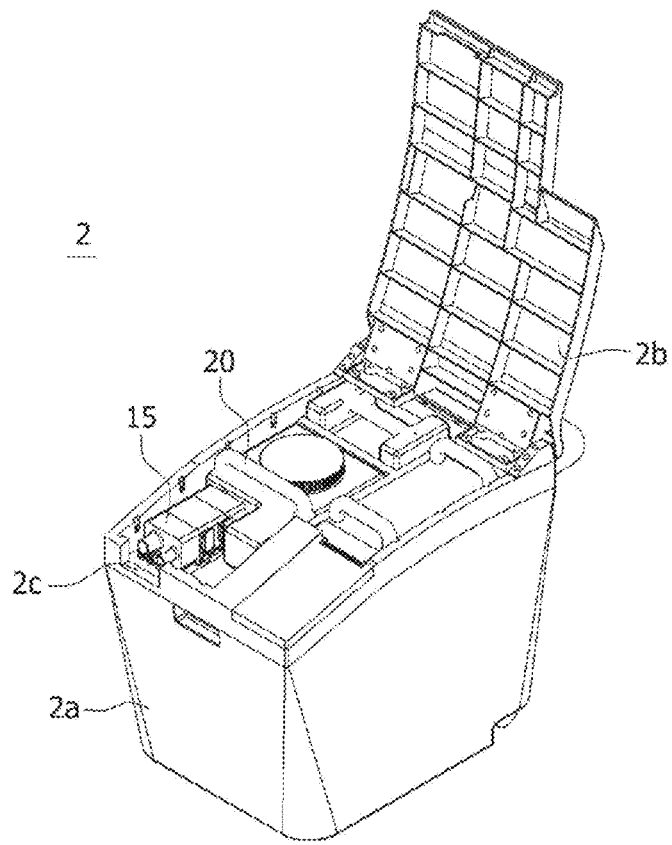
FIG. 4 is a perspective view illustrating a control device unit of the present invention.
Figure 5:
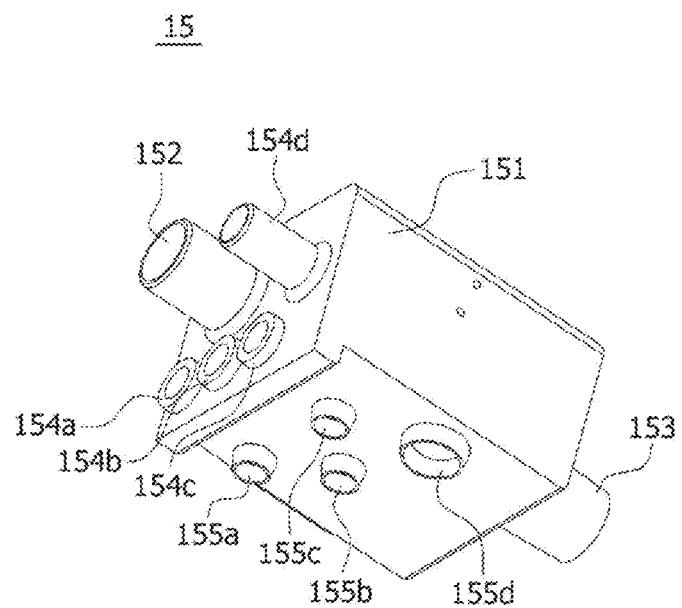
FIG. 5 is a perspective view illustrating a path connection member illustrated in FIG. 4.

FIG. 4 is a perspective view illustrating the control device unit of the present invention, and FIG. 5 is a perspective view illustrating the path connection member illustrated in FIG. 4.

Referring to FIG. 4, the control device unit 2 includes a case 2a in which constituent components, such as the excrement storage unit 20, the filter unit 30, the excrement suction unit 40, and the washing water supply unit 50, are accommodated therein, and a cover 2b covering an upper part of the case 2a. A recess 2c is formed at one side of an upper end portion of the case 2a, and the plurality of tubes 61, 62, 63, and 64 passes through the recess 2c.

A path connection member 15 in which plurality of tubes 61, 62, 63, and 64 are connected to form the path of the washing water and the air and the excrement therein is installed at an inward side of the recess 2c.

Referring to FIG. 5, an excrement inlet 152 connected with the excrement suction line 61, and washing water and air couplers 154a, 154b, 154c, and 154d connected to the washing water supply line 62, the bidet nozzle line 63, and the washing air supply line 64, respectively, protrudes from a front surface of a body 151 of the path connection member 15.

An excrement outlet 153 through which the excrement introduced from the excrement inlet 152 is discharged is formed on a rear surface of the body 151 of the path connection member 15, and a plurality of protrusions 155a, 155b, 155c, and 155d for forming air and washing water paths protrudes from a lower surface of the body 151 of the path connection member 15.

The excrement suction line 61, the washing water supply line 62, the bidet nozzle line 63, and the washing air supply line 64 connected to the couplers 101, 102, 103, 104, and 105 of the path connection unit 100 are detachably and separably coupled to the excrement inlet 152 and the couplers 154a, 154b, 154c, and 154d formed on the front surface of the path connection member 15.

The washing water and air couplers 154a, 154b, 154c, and 154d and the protrusions 154a, 154b, 154c, and 154d are communicated inside the path connection member 15.

Hereinafter, a configuration of the washing water supply unit 50 connected to the path connection member 15 will be described.

Figure 6:
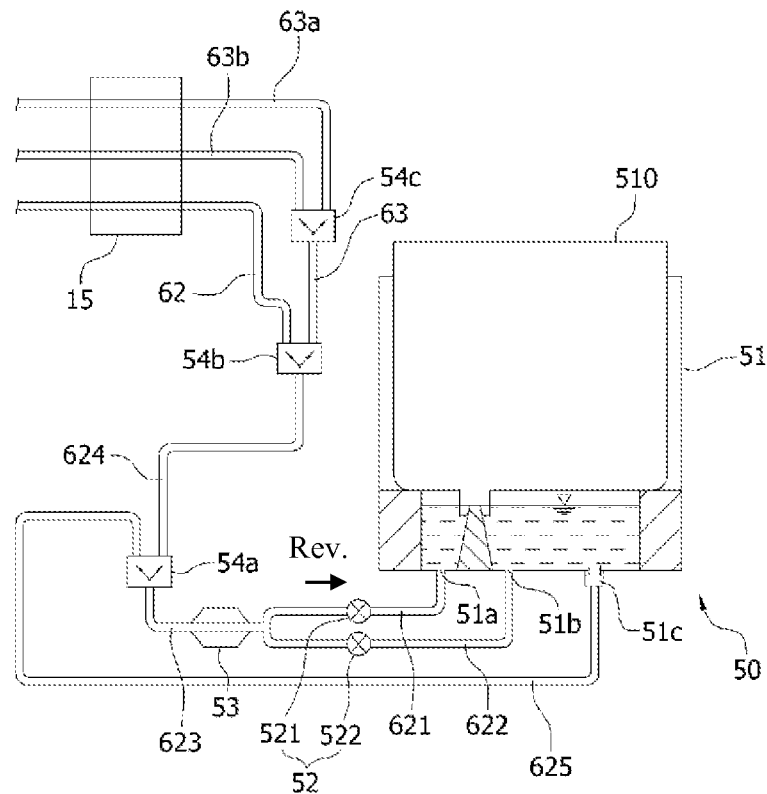
FIG. 6 is a view illustrating a washing water supply unit and a supply path and a collection path of washing water of the present invention.
Figure 7:
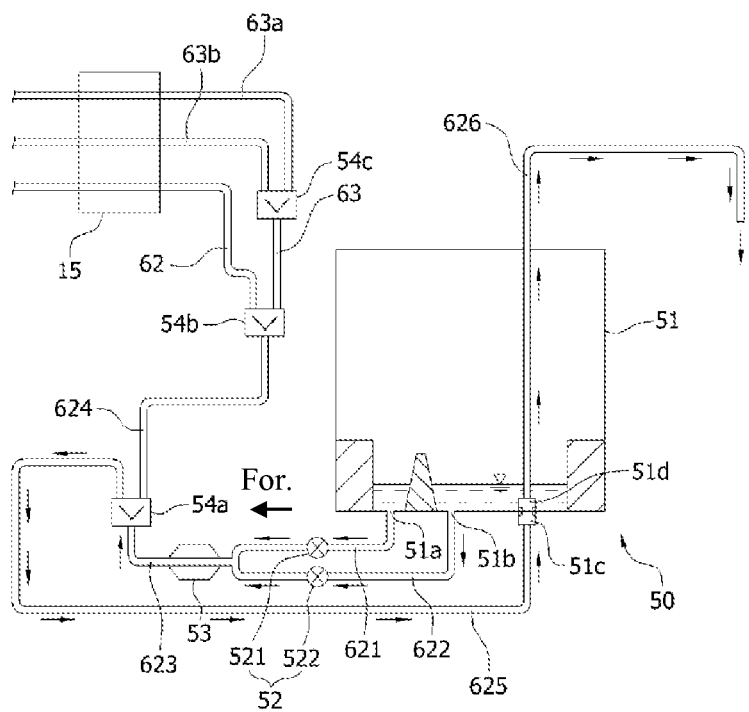
FIG. 7 is a view for describing a process of performing a drainage processing on washing water inside a washing water storage tank in an apparatus for automatically treating excrement according to the present invention.

FIG. 6 is a view illustrating the washing water supply unit and a supply path and a collection path of the washing water of the apparatus for automatically treating excrement according to the present invention, and FIG. 7 is a view for describing a process of performing a drainage processing on the washing water inside a washing water storage tank in the apparatus for automatically treating excrement according to the present invention.

Referring to FIG. 6, the washing water supply unit 50 of the present invention includes a washing water storage tank 51 in which the washing water is stored, a pump 52 operated in a forward direction or a reverse direction so as to pressurize and supply the washing water of the washing water storage tank 51 toward the mounting unit 1 or collect the residual washing water within the washing water supply path, and an instantaneous water heater 53 for heating the washing water that is pressurized by the pump 52 and supplied toward the mounting unit 1.

Here, the "washing water supply path" designates all paths of the washing water connected from the washing water storage tank 51 of the washing water supply unit 50 to the mounting unit 1.

The washing water storage tank 51 may be configured such that a water tank 510 storing the washing water is inserted upside down so that a stopper thereof heads down, and thus an inside lower part of the washing water storage tank 51 is filled with the washing water. Two inlet and outlet 51a and 51b through which the washing water passes are formed on a bottom surface of the washing water storage tank 51, and are connected to a first washing water supply line 621 and a second washing water supply line 622, respectively.

Pumps 52 (521 and 522) are installed in the first washing water supply line 621 and the second washing water supply line 622. In the present invention, the two pumps 52 are arranged in parallel, so that a gushing pressure of the washing water is increased, thereby increasing washing efficiency, compared to a case in which one pump is disposed in the related art.

The first washing water supply line 621 and the second washing water supply line 622 are connected to a third washing water supply line 623, and a first valve 54a for switching a supply path of the washing water to a fourth washing water supply line 624 or a drain line 625 is installed at an end portion of the third washing water supply line 623.

The drain line 625 is connected from the first valve 54a to the washing water storage tank 51, and a drain coupler 51c formed at an end portion thereof is fixedly installed while penetrating a bottom surface of the washing water storage tank 51.

As illustrated in FIG. 6, a connector 51d of a drain connection line 626 extending from an inside to an outside of the washing water storage unit 51 during performing the drainage processing on the washing water stagnant in the washing water storage tank 51 may be detachably coupled to the drain coupler 51c.

The instantaneous water heater 53 is installed on the third washing water supply line 623 to heat the washing water supplied toward the mounting unit 1 by the pumps 52. The instantaneous water heater 53 may be installed on the fourth washing water supply line 624.

A second valve 54b for switching the supply path of the washing water to the washing water supply line 62 or the bidet nozzle line 63 is installed at an end portion of the fourth washing water supply line 624.

The washing water supply line 62 is connected to the coupler 103 of the mounting unit 1 via the protrusion 155c and the coupler 154c of the path connection member 15.

The bidet nozzle line 63 includes a third valve 54c at an end portion thereof, so that the bidet nozzle line 63 is branched into a first bidet nozzle line 63a and a second bidet nozzle line 63b having different vertical spray heights and connected to the first coupler 101 of the mounting unit 1 via the protrusion 155a and the coupler 154a of the path connection member 15.

In the meantime, the control device unit 2 includes a controller (not illustrated) for controlling a forward directional or reverse directional operation of the pumps 52 and a switching direction in each of the first to third valves 54a, 54b, and 54c according to an operation mode of the apparatus for automatically treating excrement.

Hereinafter, a bidet washing method using the apparatus for automatically treating excrement configured as described above will be described.

When excrement is detected by a sensor (not illustrated) included in the excrement receiving unit 10 inside the mounting unit 1, the controller operates the pumps 52 in a forward direction to supply washing water for washing the excrement and the bidet toward the mounting unit 1.

In this case, an opening/closing direction of the first valve 54a is set so that the third washing water supply line 623 is connected to the fourth washing water supply line 624, an opening/closing direction of the second valve 54b is set so that the fourth washing water supply line 624 is connected to the washing water supply line 62 or the fourth washing water supply line 624 is connected to the bidet nozzle line 63 for a predetermined time, and in a state where the second valve 54b is set so as to be connected toward the bidet nozzle line 63, an opening/closing direction of the third valve 54c is set so that the bidet nozzle line 63 is connected to the first bidet nozzle line 63a or the bidet nozzle line 63 is connected to the second bidet nozzle line 63b for a predetermined time.

Accordingly, the washing water of the washing water storage tank 51 is supplied to the washing water spray nozzle 11 and the bidet nozzles 12a and 12b of the mounting unit 1 to perform the excrement washing and the bidet washing.

After an excrement treating operation including the excrement washing and the bidet washing is completed, the controller controls the pumps 52 to collect the residual washing water in the washing water supply path before the instantaneous water heater 53 by operating the pumps 52 in a reverse direction for a set time. When the collection of the washing water is completed, a standby state is continued until excrement is detected later, and when excrement is detected in the mounting unit 1, the aforementioned process is repeatedly performed.

As described above, in the present invention, when the excrement is washed and the bidet is washed, the washing water is in a collected state before the instantaneous water heater 53, so that when the pumps 52 are operated in the forward direction that is a supply direction of the washing water, the washing water collected in the washing water supply path before the instantaneous water heater 53 and the washing water inside the washing water storage tank 51 is heated to a warm state via the instantaneous water heater 53 to be supplied toward the mounting unit 1.

Accordingly, the bidet washing may be performed by the warm washing water heated via the instantaneous water heater 53 from the initial washing operation in the bidet, so that it is possible to resolve a problem of giving an unpleasant feeling to a user due to the supply of cold water at an initial washing stage in a bidet in the related art.

In the meantime, the controller may be configured so as to stop an operation of the apparatus through an manipulation of a separate switching means (not illustrated) in a state where the residual washing water in the washing water supply path is collected in the initial washing stage in the bidet, and in this case, even though the plurality of connection tubes 61, 62, 63, and 64 fastened to the path connection member 15 is separated, the washing water may be prevented from being poured.

Hereinafter, a method of draining the residual washing water inside the washing water storage tank by using the apparatus for automatically treating excrement will be described with reference to FIG. 7.

When the apparatus for automatically treating excrement is stored without being used for a long time, it is necessary to perform a drainage processing on the washing water stored inside the washing water storage tank 51.

In this case, when the water tank 510 inserted in the washing water storage tank 51 is withdrawn to the outside, the washing water is stagnant at a bottom inside the washing water storage tank 51.

In this state, the connector 51d of the drain connection line 626 is fastened to the drain coupler 51c of the drain line 625 installed so as to pass through the bottom of the washing water storage tank 51. An opposite end portion of the connector 51d of the drain connection line 626 may be connected to a separate container for receiving the drained washing water or a drain.

In a next step, when a washing water drainage mode is operated, in the first valve 54a, the flow path is set so that the path of the washing water heads from the third washing water supply line 623 to the drain line 625, and when the pumps 52 are operated in the forward direction, the washing water stagnant inside the washing water storage tank 51 is drain-processed to the outside of the washing water storage tank 51 sequentially via the first and second washing water supply lines 621 and 622, the pumps 52, the third washing water supply line 623, the drain line 625, and the drain connection line 626.

As described above, the drain line 625 is installed so as to be connected from the first valve 54a to the bottom of the washing water storage tank 51, and the connector 51d of the drain connection line 626 is coupled to the drain coupler 51c of the drain line 625 during the drainage processing, so that the drainage processing may be easily performed on the washing water inside the washing water storage tank 51.

Hereinafter, a structure of the filter unit according to the present invention will be described with reference to FIGS. 8 to 15.

Figure 8:
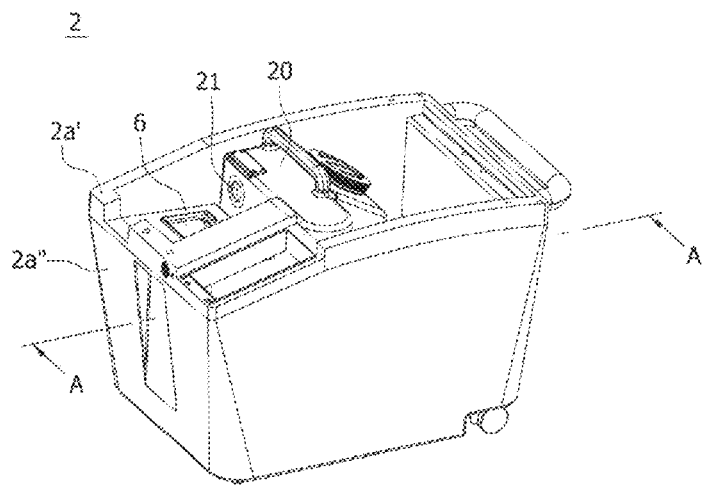
FIG. 8 is an exterior perspective view of a control device unit of the present invention.
Figure 9:
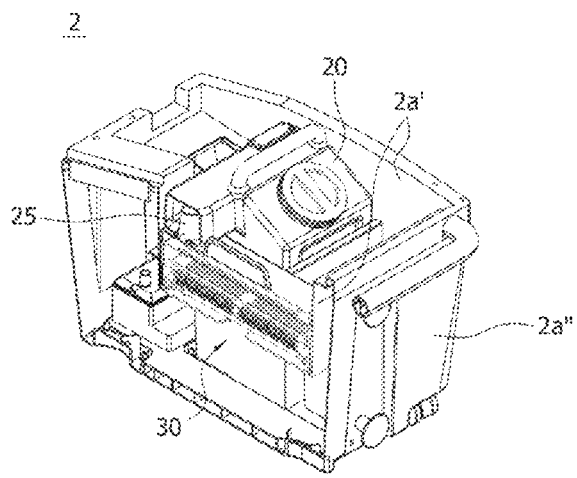
FIG. 9 is a cross-sectional view taken along A-A of FIG. 2.

FIG. 8 is a perspective view of an exterior of the control device unit of the present invention, and FIG. 9 is a cross-sectional view taken along A-A of FIG. 8.

The control device unit 2 includes an upper case 2a' provided with a space in which the constituent components, such as the excrement storage unit 20 and the filter unit 30, are accommodated, and a lower case 2a" assembled with a lower part of the upper case 2a' to configure an exterior of the control device unit 2 and accommodating the constituent components, such as the excrement suction unit 40 and the washing water supply unit 50 therein.

A path coupler 6 through which the washing water supply line 62, the bidet nozzle line 63, and the washing air supply line 64 illustrated in FIG. 1 pass is formed at one side of the upper case 2a', and an excrement path coupler 21 in which the excrement flows is formed at one side of the excrement storage unit 20 accommodated closely to the path coupler 6.

Polluted air in the internal space of the excrement storage unit 20 is sucked to the filter unit 30 through the coupler 25 formed at one side of an upper part of an inner side of the excrement storage unit 20.

Figure 10:
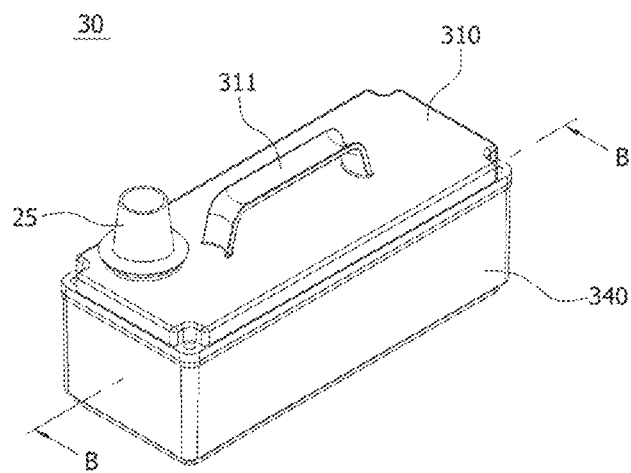
FIGS. 10 and 11 are perspective views of a filter unit of the present invention.
Figure 11:
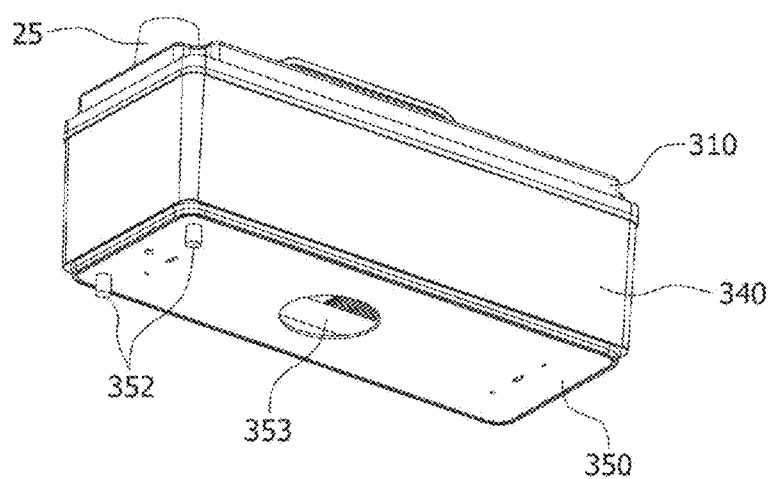
Figure 12:
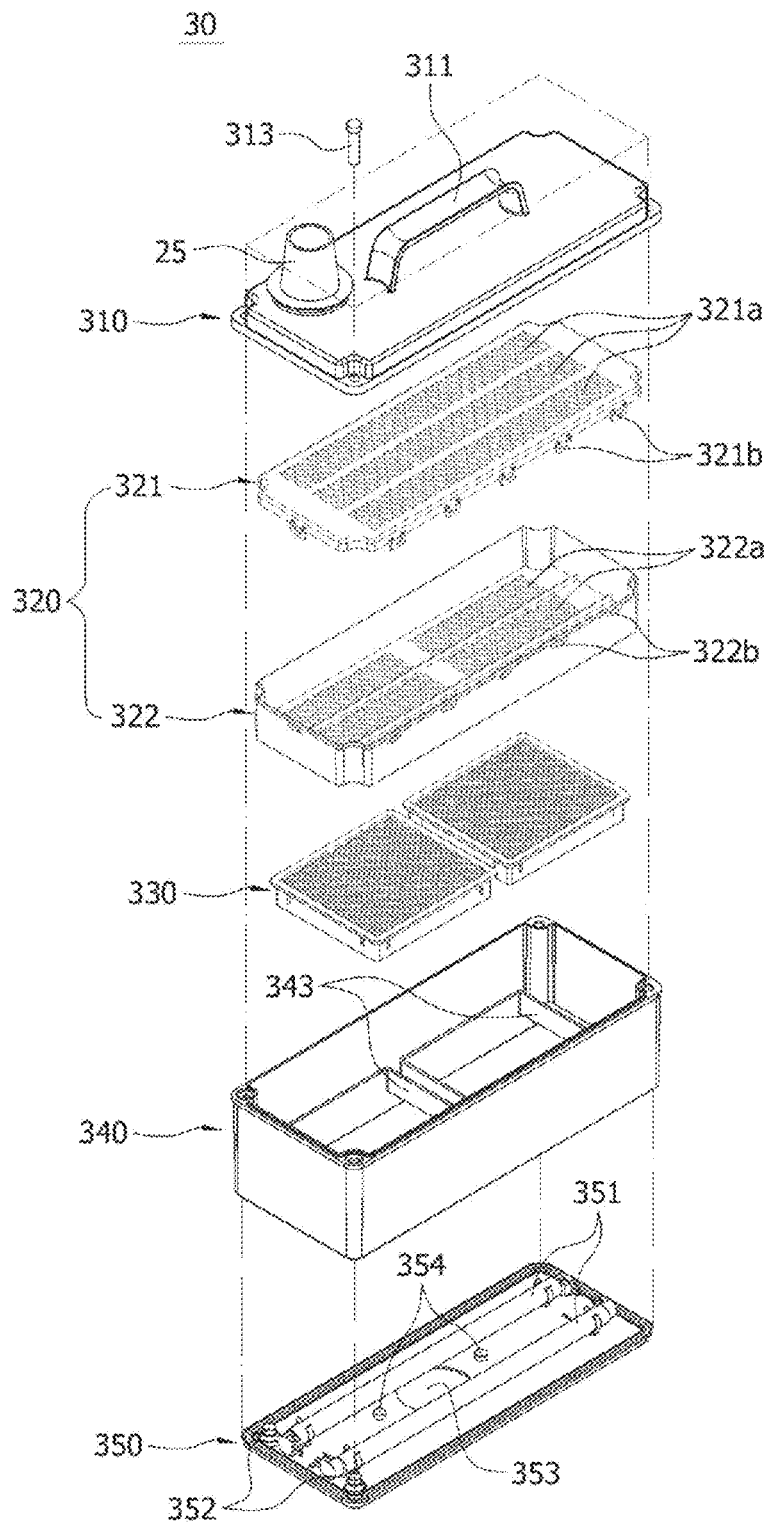
FIG. 12 is an exploded perspective view of a filter unit of the present invention.

FIGS. 10 and 11 are perspective views of the filter unit of the present invention, and FIG. 12 is an exploded perspective view of the filter unit of the present invention.

The apparatus for automatically treating excrement of the present invention is characterized by including the filter unit 30 which minimizes a used load of the pump of the excrement suction unit 40 and the motor for driving the pump in a process of sucking the excrement and the air of the mounting unit 1, storing the excrement in the excrement storage unit 20, and purifying and circulating the polluted air in the internal space of the excrement storage unit 20 by making the polluted air pass through the filter unit 30, and has an easily assemblable/disassemblable structure.

Referring to FIGS. 10 and 11, the filter unit 30 is characterized in that an entire shape thereof has a wider transverse sectional area perpendicular to the path direction of the air connected from the upper coupler 25 to a lower air outlet 353 than a longitudinal sectional area parallel to the path direction.

In this case, a length of the path direction of the air is formed to be short, so that it is possible to decrease a loss of pressure of the air passing between the coupler 25 of the filter unit 30 and the air outlet 353 and reduce a load of the excrement suction unit 40. Further, the deterioration of the filtering performance caused by the decrease of the time for which the air passes through the inside of the filter unit 30 may be compensated for by forming the wide transverse sectional area and sufficiently securing a contact area with the air.

Referring to FIG. 12, the filter unit 30 includes an upper cover 310 including the coupler 25 and a grip portion 311 formed on an upper part thereof, a first filter unit 320 filled with activated carbon to filter pollutants while the air introduced through the coupler 25 passes through the first filter unit 320 therein, a second filter unit 330 for filtering dust of the activated carbon contained in the air passing through the first filter unit 320, a main body 340 having an upper part opened/closed by the upper cover 310, accommodating the first filter unit 320 and the second filter unit 330 therein, and having an opened lower part, and a bottom frame 350 having an upper surface on which the main body 340 is seated and including ultraviolet lamps 351 for sterilizing the air passing through the second filter unit 330.

The air sucked through the coupler 25 of the upper cover 310 as described above goes through a sterilizing process by light emission of the ultraviolet lamps 351 after the pollutants and bad smell are removed while sequentially passing the first filter unit 320 and the second filter unit 330, and then discharged to the excrement suction unit 40 through the air outlet 353 of the bottom frame 350.

The first filter unit 320 is vertically separated so that an upper slit member 321 is detachably coupled to a lower slit member 322.

A plurality of "U" shaped fastening members 321b is formed at a circumference of a side of the upper slit member 321 by intervals, and a plurality of protrusions 322b detachably coupled to the fastening members 321b may be formed in a circumference of an upper part of the lower slit member 322.

Figure 14:
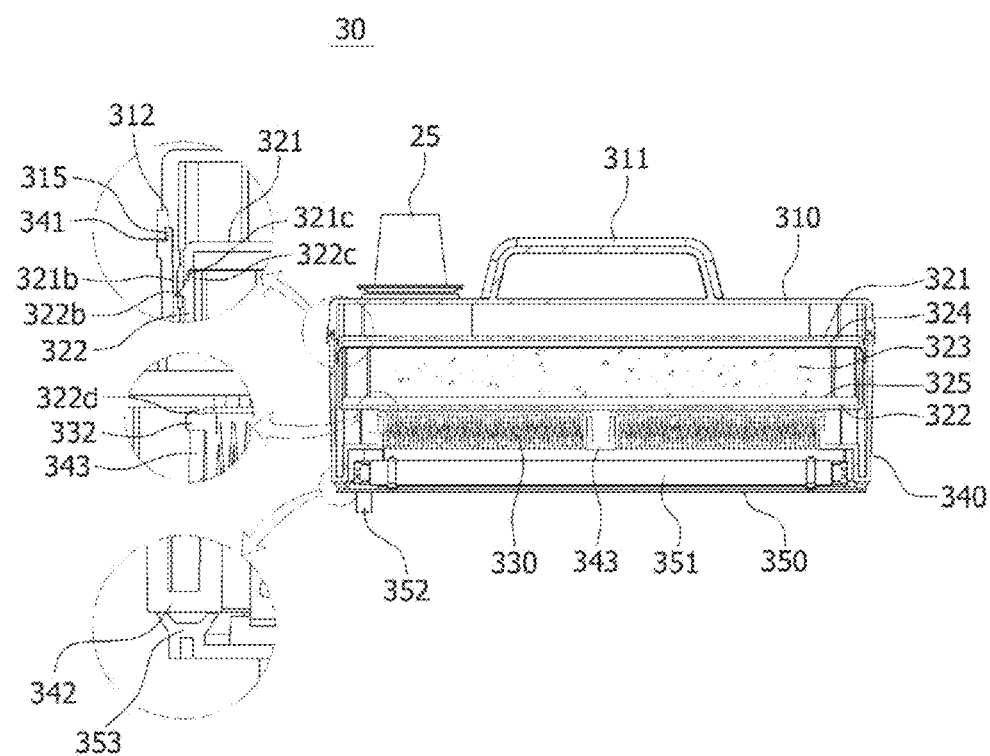
Figure 15:
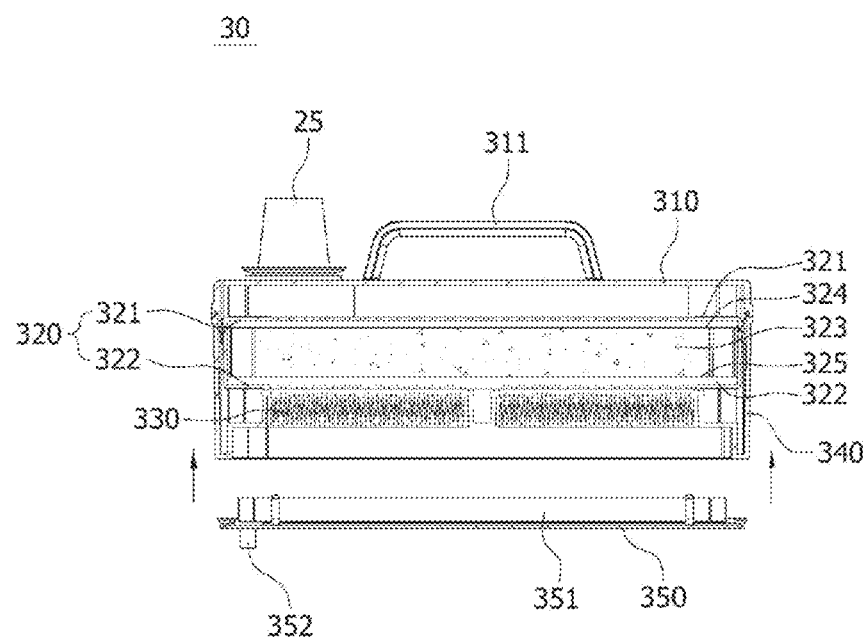
FIG. 15 is an in-use state view for describing a process of replacing a filter unit according to the present invention.

A plurality of slits 321a and 322a is densely formed in the upper slit member 321 and the lower slit member 322, and an inside of the lower slit member 322 is filled with activated carbon 323 surrounded by nonwoven fabrics 324 and 325 (see FIG. 14). Accordingly, the pollutants contained in the air passing through the upper slit member 321 are collected while passing through the activated carbon 323 filled inside the lower slit member 322 having a structure of a wide transverse area at a low speed, and the air in which the pollutants are removed passes through the slit 322a formed on the bottom surface of the lower slit member 322 and flows in the second filter unit 330 formed at a lower side.

The second filter unit 330 is for filtering fine dust of the activated carbon 323 contained in the air passing through the first filter unit 320, and may be installed so that a HEPA filter shaped like a thin filter paper is wrinkled and connected in a vertical direction so as to increase a contact area with the air.

The first filter unit 320 and the second filter unit 330 are accommodated up and down inside the main body 230, the upper cover 10 and edge portions of an upper border of the main body 340 are coupled by coupling members 313, such as screws, while being penetrated upward and downward, and the main body 340 is seated on an upper surface of the bottom frame 350.

The ultraviolet lamps 351 for sterilization and a wiring for supplying power are mounted in the bottom frame 350, and switch units 352 for automatically turning on or off power supplied to the ultraviolet lamps 351 according to the coupling/separation of the main body 340 and the bottom frame 350 are included in the bottom frame 350.

That is, in a state where the main body 340 is seated on the bottom frame 350, a pressing portion of an upper end of the switch unit 352 at a lower end of the main boy 340 is pressed downward, so that power connection terminals are electrically connected and thus the power supplied to the ultraviolet lamp 351 becomes an ON state, and in a state where the main body 340 is separated from the bottom frame 350, the pressing portion of the switch unit 352 is move upward, so that the power connection terminals are disconnected and thus the power supplied to the ultraviolet lamp 351 becomes an OFF state.

As described above, the ultraviolet lamp 351 is configured so as to be automatically turned off when grasping a grip portion 311 of the upper cover 310 and lifting the main body 340 coupled by the coupling members 313 toward the upper side of the bottom frame 350 in order to replace the constituent component inside the filter unit 30, so that damage to a body caused by direct exposure of light of the ultraviolet ray lamp 351 to the eyes of an operator may be automatically prevented in advance.

Further, a pressure sensor 354 for measuring a degree of vacuum of air may be included inside the filter unit 30, for example, the bottom frame 350. The block or leakage of the sucked air flow may be determined based on the degree of vacuum measured by the pressure sensor 354.

Hereinafter, a coupling structure between the constituent components of the filter unit 30 will be described.

Figure 13:
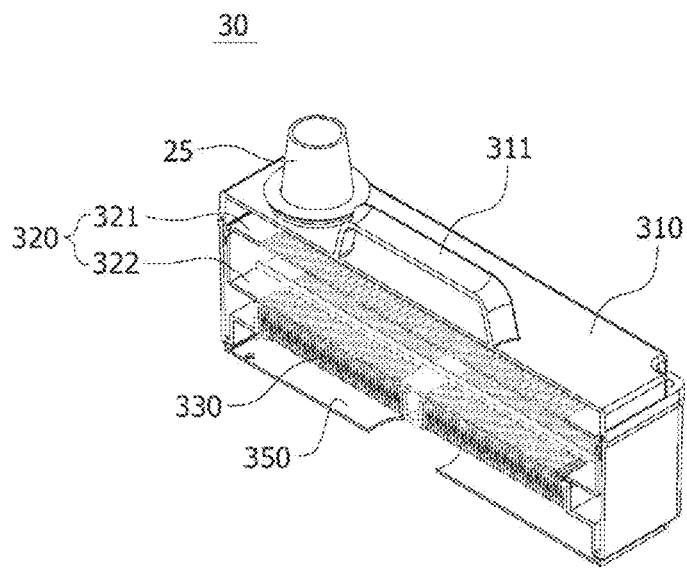
FIGS. 13 and 14 are a cut perspective view and a cross sectional view taken along B-B of FIG. 10.

FIGS. 13 and 14 are a cut perspective view and a cross sectional view taken along B-B of FIG. 10.

First, in a coupling structure between the upper cover 310 and the main body 340, in addition to the coupling by the coupling members 313 penetrating vertically the edge portions of the border at which a lower end portion of the upper cover 310 is in contact with an upper end portion of the main body 340 as described above, in order to maintain sealing in a coupled state, a seating recess 312 is formed at a border of the lower end of the upper cover 310 and a seated protrusion 341 inserted in the seating recess 312 is formed at a border of the upper end of the main body 340. Further, a sealing member 315 is interposed inside the seating recess 312 and the sealing member 315 is compressed against an upper end of the seated protrusion 341, so that the sealing at a connection portion between the upper cover 310 and the main body 340 is maintained.

Next, in a coupling structure between the upper slit member 321 and the lower slit member 322 of the first filter unit 320, in addition to the coupling between the fastening member 321b formed at the circumference of the side of the upper slit member 321 and the protrusion 322b formed at the circumference of the upper portion of the lower slit member 322 as described above, fitted units 321c and 322c in which a protrusion and an insertion recess having matched shapes are cross-coupled to each other may be formed at a border of a lower end of the upper slit member 321 and a border of an upper end of the lower slit member 322.

In describing a structure in which the first filter unit 320 and the second filter unit 330 are accommodated inside the main body 340, a holding portion 343 in which a flange portion 332 protruding from a border of the upper end of the second filter unit 330 in a lateral direction is seated is formed inside the main body 340, so that the second filter unit 330 is laid on an upper end of the holding portion 343.

Further, a protrusion 322d protruding downward so as to be in contact along an upper surface of the flange portion 332 of the second filter unit 330 is formed on a lower surface of the first filter unit 320, so that the sealing between a border of a lower surface of the first filter unit 320 and the flange portion 332 of the second filter unit 330 is maintained. Accordingly, the air flowing inside the main body 340 through the coupler 25 at an upper part of the filter unit 30 is prevented from first flowing in the second filter unit 330 without passing through the first filter unit 320, and the path is formed so that the air sequentially passes through the first filter unit 320 and the second filter unit 330.

As described above, in the present invention, the second filter unit 330 is held on the holding portion 343 without a separate fastening means and the first filter unit 320 is laid on the second filter unit 330, so that the first filter unit 320 and the second filter unit 330 may be easily accommodated inside the main body 340, and further a leakage of air from a gap of a connected portion may be effectively prevented.

In the meantime, in describing the coupling structure between the main body 340 and the bottom frame 350, a flat lower contact portion 342 having a predetermined width is formed at a border of a lower end of the main body 340, and a main body seating portion 353 made of an elastic material, such as rubber, shaped like a letter "Y" in which the lower contact portion 342 is seated is formed at a border of the bottom frame 350. Accordingly, when the lower contact portion 342 of the main body 340 is seated on the main body seating portion 353 of the bottom frame 359, an upper portion of the main body seating portion 353 is pressurized and elastically deformed by a load of the main body 340, so that the lower contact portion 342 is in close contact with the main body seating portion 353.

FIG. 7 is an in-use state view for describing a process of replacing the filter unit according to the present invention.

When an operator grasps and lifts up the grip portion 311 of the upper cover 310 in order to replace the constituent component inside the filter unit 30, the upper cover 310 and the main body 340 coupled by the coupling members 313 and the first filter unit 320 and the second filter unit 330 accommodated inside the main body 340 are lifted up together, to be separated from the bottom frame 350.

Simultaneously, the power connection is blocked by the switch unit 352, so that the ultraviolet lamp 351 is turned off as described above.

As described above, after the upper cover 310 and the main body 340 are withdrawn outside the apparatus for automatically treating excrement, the first filter unit 320 and the second filter unit 330 are easily separated by only an operation of disjointing the coupling members 313 fastened between the upper cover 310 and the main body 340 and lifting up the first filter unit 320 and the second filter unit 330 accommodated inside the main body 340, so that the component may be replaced with a new component.

INDUSTRIAL APPLICABILITY

The apparatus for automatically treating excrement and the controlling method thereof provided in the present invention can supply heated warm washing water from an initial washing operation in a bidet, reduce a load of a pump used for sucking excrement and air, and improve filtering performance, thereby having an advantage for the industrial applicability.

The invention claimed is:

1. An apparatus for automatically treating excrement comprising a mounting unit configured to receive excrement of a patient, a control device unit including a washing water supply unit configured to supply washing water to a bidet in the mounting unit, and a washing water supply path connecting the washing water supply unit to the mounting unit, the washing water supply unit including:
    a washing water storage tank storing the washing water;
    a reversible pump operating in a forward direction when pumping the washing water from the washing water storage tank to the mounting unit, and in a reverse direction when pumping residual washing water in the washing water supply path to the washing water storage tank;
    an instantaneous water heater provided on the washing water supply path, the instantaneous water heater heating the washing water pumped to the mounting unit; and
    a controller configured to operate the pump in the forward direction or the reverse direction,
    wherein, when excrement is sensed in the mounting unit, the controller begins a treatment operation by operating the reversible pump in the forward direction such that the washing water is emitted from the bidet, and
    wherein, when the treatment operation is completed, the controller begins a collection operation by operating the reversible pump in the reverse direction for a set time, such that the residual washing water is collected in the washing water storage tank.

2. The apparatus for automatically treating excrement of claim 1, wherein the pump includes a plurality of pumps arranged in parallel.

3. The apparatus for automatically treating excrement of claim 1, further comprising:
    a drain line; and
    a first valve coupled between the instantaneous water heater, the drain line, and the mounting unit,
    wherein, when the first valve connects the instantaneous water heater to the drain line, the pump operating in the forward direction pumps washing water from the washing water storage tank through the instantaneous water heater and out the drain line.

4. The apparatus for automatically treating excrement of claim 3, wherein a drain coupler attached to a first end of the drain line, opposite to a second end connected to the valve, the drain coupler penetrating a bottom surface of the washing water storage tank, the drain coupler being coupled to a connector of a drain connection line that extends from the washing water storage tank.

5. The apparatus for automatically treating excrement of claim 1, further comprising an excrement receiving unit for receiving the excrement of the patient, an excrement storage unit configured to suck the excrement of the excrement receiving unit through an excrement suction line and then store the sucked excrement, a filter unit connected to the excrement storage unit and configured to purify sucked air, and an excrement suction unit connected to the filter unit and configured to provide a suction force that sucks the excrement,
    wherein the filter unit comprises:
        an upper cover including a coupler connected to the excrement storage unit;
        a first filter unit filled with activated carbon that collects pollutants from air introduced through the coupler;
        a second filter unit configured to filter dust of the activated carbon contained in air passing through the first filter unit;
        a main body having an upper part opened and closed by the upper cover, the main body housing the first filter unit and the second filter unit therein, the main body having an opened lower part; and a bottom frame on which the main body is seated, the bottom frame comprising an ultraviolet lamp sterilizing the air passing through the second filter unit.

6. The apparatus for automatically treating excrement of claim 5, wherein the first filter unit has a wider transverse sectional area perpendicular to the direction of the path of the air introduced through the coupler than a longitudinal sectional area parallel to the direction of the path.

7. The apparatus for automatically treating excrement of claim 6, wherein the first filter unit separately comprises a lower slit member filled with the activated carbon, and an upper slit member detachably coupled to an upper portion of the lower slit member, and a plurality of slits formed in the upper slit member and the lower slit member, the plurality of slits communicating vertically.

8. The apparatus for automatically treating excrement of claim 5, wherein a seating recess and a seated protrusion inserted in the seating recess are formed at a border at which the upper cover is coupled to the main body, coupling members are coupled to edge portions of the border while vertically penetrating the edge portions of the border, and a grip portion is provided at an upper part of the upper cover.

9. The apparatus for automatically treating excrement of claim 5, wherein the first filter unit is seated on the second filter unit, and a protrusion protrudes downward from a border of a lower surface of the first filter unit to seal a border of a lower surface of the first filter unit and a flange portion of the second filter unit, the protrusion contacting an upper surface of the flange portion formed at a border of an upper end of the second filter unit.

10. The apparatus for automatically treating excrement of claim 5, wherein a flat lower contact portion having a predetermined width is disposed at a border of a lower end of the main body, and a Y-shaped main body seating portion and made of a rubber material, in which the lower contact portion is seated, is disposed at a border of the bottom frame.

11. The apparatus for automatically treating excrement of claim 5, wherein the bottom frame comprises switch units configured to turn on power supplied to the ultraviolet lamp in a state where the main body is seated on the bottom frame, and turn off the power supplied to the ultraviolet lamp in a state where the main body is separated from the bottom frame.

12. The apparatus for automatically treating excrement of claim 5, wherein a pressure sensor configured to measure a degree of vacuum of the air is located inside of the filter unit.

13. A method of controlling an apparatus for automatically treating excrement that includes a mounting unit for receiving excrement of a patient, a control device unit including a washing water supply unit configured to supply washing water to a bidet on the mounting unit, and a washing water supply path connected from the washing water supply unit to the mounting unit, the method comprising:

treating excrement by operating, by a controller, a reversible pump included in the washing water supply unit in a forward direction such that the washing water is emitted from the bidet; and operating, by the controller, the reversible pump in a reverse direction opposite to the forward direction for a set time after the excrement has been treated, such that residual washing water in the washing water supply path is collected in the washing water storage tank, wherein the forward direction is a supply direction.

14. The method of controlling an apparatus for automatically treating excrement of claim 13, further comprising:

operating, by the controller, the reversible pump in the forward direction when the excrement is detected in the mounting unit after the residual washing water is collected, thereby supplying washing water to the mounting unit, the supplied washing water including the collected residual washing water and the washing water within the washing water storage tank; and heating the supplied washing water by passing the supplied washing water through instantaneous water heater.

15. The apparatus for automatically treating excrement of claim 10, wherein the bottom frame comprises switch units configured to turn on power supplied to the ultraviolet lamp when the main body is seated on the bottom frame, and turn off the power supplied to the ultraviolet lamp when the main body is separated from the bottom frame.

16. The apparatus for automatically treating excrement of claim 1, wherein the instantaneous water heater is coupled between the pump and the mounting unit.

17. An apparatus, comprising:
an excrement receiving unit;
an excrement tank coupled between the excrement receiving unit and a vacuum pump;
a water storage tank storing washing water;
a reversible pump coupled between the water storage tank and the excrement receiving unit, the reversible pump configured to pump the washing water out of the water storage tank when operating in a forward direction, and to pump residual water into the water storage tank when operating in a reverse direction;
a controller configured to operate the reversible pump in the forward direction or the reverse direction; and
an instantaneous water heater coupled between the reversible pump and the excrement receiving unit,
wherein, when excrement is sensed in the mounting unit, the controller begins a treatment operation by operating the reversible pump in the forward direction such that the washing water is emitted from the bidet, and
wherein, when the treatment operation is completed, the controller begins a collection operation by operating the reversible pump in the reverse direction for a set time, such that the residual washing water is collected in the washing water storage tank.

18. The apparatus of claim 17, further comprising:
a drain connection line; and
a valve selectively connecting a line from the water storage tank and through the pump to the drain connection line or a line connected to the excrement receiving unit.

* * * * *